US007258878B2

(12) United States Patent
Greene et al.

(10) Patent No.: US 7,258,878 B2
(45) Date of Patent: Aug. 21, 2007

(54) ANTI-MICROBIAL COMPOSITION AND METHODS OF USE THEREOF

(75) Inventors: Sharon Linda Greene, Canton, GA (US); Yanbin Huang, Foster City, CA (US); Lei Huang, Duluth, GA (US); Ilona F. Weart, Woodstock, GA (US); Shu-Ping Yang, Alpharetta, GA (US); Sohail Malik, Athens, GA (US); Robert B. Johnson, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 11/017,226

(22) Filed: Dec. 20, 2004

(65) Prior Publication Data

US 2006/0134237 A1    Jun. 22, 2006

(51) Int. Cl.
A61K 36/752    (2006.01)
(52) U.S. Cl. ........................ 424/736; 435/149; 424/725
(58) Field of Classification Search ...................... None
See application file for complete search history.

(56) References Cited

U.S. PATENT DOCUMENTS

| 4,732,797 | A | 3/1988 | Johnson et al. |
| 4,772,501 | A | 9/1988 | Johnson et al. |
| 4,941,996 | A | 7/1990 | Trend et al. |
| 4,966,724 | A | 10/1990 | Culshaw |
| 5,051,212 | A | 9/1991 | Culshaw et al. |
| 5,145,839 | A * | 9/1992 | Beljanski ............... 514/27 |
| 5,158,774 | A | 10/1992 | Inman |
| 5,230,823 | A | 7/1993 | Wise et al. |
| 5,348,682 | A | 9/1994 | Finley et al. |
| 5,382,376 | A | 1/1995 | Michael et al. |
| 5,397,494 | A | 3/1995 | Vega et al. |
| 5,429,773 | A | 7/1995 | Sherry et al. |
| 5,475,134 | A | 12/1995 | Baker |
| 5,514,294 | A | 5/1996 | Bohnert et al. |
| 5,536,450 | A | 7/1996 | Masters et al. |
| 5,536,451 | A | 7/1996 | Masters et al. |
| 5,545,340 | A | 8/1996 | Wahl et al. |
| 5,545,350 | A | 8/1996 | Baker et al. |
| 5,574,179 | A | 11/1996 | Wahl et al. |
| 5,587,358 | A | 12/1996 | Sukigara et al. |
| 5,663,152 | A | 9/1997 | Hayanno et al. |
| 5,679,631 | A | 10/1997 | Bohnert et al. |
| 5,688,982 | A | 11/1997 | Khan et al. |
| 5,703,033 | A | 12/1997 | Sherry et al. |
| 5,703,036 | A | 12/1997 | Inkovides |
| 5,776,919 | A | 7/1998 | Sukigara et al. |
| 5,814,590 | A | 9/1998 | Sherry et al. |
| 5,972,431 | A | 10/1999 | Marsella et al. |
| 5,985,968 | A | 11/1999 | Lassila et al. |
| 6,096,225 | A | 8/2000 | Yang et al. |
| 6,096,349 | A | 8/2000 | Petri et al. |
| 6,110,888 | A | 8/2000 | Lupo, Jr. et al. |
| 6,124,374 | A | 9/2000 | Kolias |
| 6,152,152 | A | 11/2000 | Reynen et al. |
| 6,179,906 | B1 | 1/2001 | Marsella et al. |
| 6,218,434 | B1 | 4/2001 | Crooks et al. |
| 6,262,156 | B1 | 7/2001 | Marsella et al. |
| 6,281,170 | B1 | 8/2001 | Marsella et al. |
| 6,288,151 | B1 | 9/2001 | Lassila et al. |
| 6,348,187 | B1 | 2/2002 | Pan et al. |
| 6,469,061 | B1 * | 10/2002 | Flescher et al. ............ 514/530 |
| 6,585,961 | B1 | 7/2003 | Stockel |
| 2002/0065340 | A1 | 5/2002 | Denesuk |
| 2003/0012804 | A1 | 1/2003 | Cutler et al. |
| 2003/0095931 | A1 | 5/2003 | Stier |
| 2003/0157193 | A1 | 8/2003 | McDonald et al. |

FOREIGN PATENT DOCUMENTS

| EP | 0496349 B1 | 4/1996 |
| EP | 0842604 A1 | 5/1998 |
| EP | 0985015 A1 | 12/1998 |
| JP | 09-040571 | 2/1997 |
| JP | 09-194358 | 7/1997 |
| WO | WO-98/54279 A1 | 12/1998 |
| WO | WO-01/60971 A2 | 8/2001 |

OTHER PUBLICATIONS

"Comprehensive Guide to Fungus and Fungal and Yeast Infections and Treatment", http://www.fungusfocus.com/html/fungus_general_info.htm, (observed Dec. 6, 2004), 7 pgs.

"Many Americans Make Eating Organic Food a Top Choice to Protect Health, According to New Survey", http://web.archive.org/web/20030302011548/http://walnutacres.com/news_view.

"Partial International Search Report for corresponding PCT Application No. PCT/US2005/025366", 2 pgs.

Bisignano, G., et al., "Antimicrobial Activity of *Mitracarpus scaber* Extract and Isolated Constituents", *Letters In Applied Microbiology*, 30(2), (Feb. 2000), 105-108.

Branna, Tom, "Innovations Drive Chemical Specialties: Even Though Sales of Cleaning Products Have Stalled, Innovation Products Still Find a Receptive Audience", *Happi-Household & Personal Products Industry*, 39(4), http://www.happi.com/current/April023.htm, Apr. 2002), 74-82.

Cho, S Y., "Opportunistic Fungal Infection Among Cancer Patients", *American Journal of Clinical Pathology*, 72(4), (Oct. 1979), 617-621. php?id=13, (archived Mar. 2, 2003), 3 pgs.

(Continued)

Primary Examiner—Christopher R. Tate
Assistant Examiner—Deborah A. Davis
(74) Attorney, Agent, or Firm—Schwegman, Lundberg, Woessner, & Kluth, P.A.

(57) ABSTRACT

The present invention is directed to anti-microbial compositions and methods for treating fungal and yeast infections.

4 Claims, No Drawings

OTHER PUBLICATIONS

Cowan, Marjorie M., "Plant Products as Antimicrobial Agents", *Clinical Microbiology Reviews*, 12(4), (1999), 564-582.

David, Hugo L., et al., "Alterations in the Outer Wall Architecture Caused by the Inhibition of Mycoside C Biosynthesis in *Mycobacterium* avium", *Current Microbiology*, 17(2), (1988), 61-68.

Denyer, S. P., "Mechanisms of Action of Antibacterial Biocides", *International Biodeterioration and Biodegration*, 36(3), (1995), 227-245.

Dixon, Dennis M., et al., "Fungal Infections—A Growing Threat", *Public Health Reports*, 11(3), (May/Jun. 1996), 226-234.

Fogliani, B., et al., "Bioactive ellagitannins from *Cunonia macrophylla*, an endemic Cunoniaceae from New Caledonia", *Phytochemistry*, 66(2), (Jan. 2005), 241-247.

Füssle, Roswitha, "Diagnosis of Fungal Infections", *Mycoses*, 40(Suppl. 2), (1997), 13-15.

Hawsawi, Zubaida A., et al., "Effect of *Nigella Sativa* (Black Seed) and Thymoquinone on Blood Glucose in Albino Rats", *Journal of Saudi Medicine*, 21(3-4), (2001), 242-244.

Hiom, Sarah J., et al., "Effects of Chlorhexidine Diacetate and Cetylpyridinium Chloride on Whole Cells and Protoplasts of *Saccharomyces cerevisiae*", *Microbios*, 74(299), (1993), 111-120.

Jansen, Christina, et al., "Where do the Leads for Licenses Come From?", *The Journal of the Association of University Technology Matters*, vol. XI, http://www.autm.net/pubs/journal/99/leads.cfm,(1999),6 pgs.

Jones, Rhonda D., et al., "Triclosan: A Review of Effectiveness and Safety in Health Care Settings", *American Journal of Infection Control*, 28(2), (Apr. 2000), 184-196.

Kim, H.-Y., et al., "Isolation of Antimicrobial Substances From Natural Products and Their Preservative Effect", *Food Sci. Biotechnol.*, 10(1), (2001), 59-71.

McDonnell, Gerald, et al., "Antiseptics and Disinfectants: Activity, Action, and Resistance", *Clinical Microbiology Reviews*, 12(1), (1999), 147-179.

Roach, John, "Why Some Like It Hot: Spices Are Nature's Meds, Scientist Says", http://news.nationalgeographic.com/news/2005/11/1111_051111_.spicy_medicine.html, 3 pgs.

Rolston, Kenneth, "Overview of Systemic Fungal Infections", *Oncology*, 15(11)(Supplement), (2001), 11-14.

Rubin, Zachary A., et al., "New Options for the Treatment of Invasive Fungal Infections", *Seminars in Oncology*, 31(2)(Supplement 4), (Apr. 2004), 91-98.

Ruhnke, M., et al., "Management of Mycoses in Patients With Hematologic Disease and Cancer—Review of the Literature", *European Journal of Medical Research*, 7, (2002), 227-235.

Salager, Jean-Louis, et al., "Nanoemulsions: Where Are They Going To?", *TPoint*, Feb. 2003, EniTechnologie Technological Bulletin,(Jun. 2003),12-14.

Sefton, Armine M., "Mechanisms of Antimicrobial Resistance—Their Clinical Relevance in the New Millennium", *Drugs*, 62(4), (2002), 557-566.

Shi, Rui, et al., "Enhanced Immune Response to Gastric Cancer Specific Antigen Peptide by Coencapsulation With CpG Oligodeoxynucleotides in Nanoemulsion", *Cancer Biology & Therapy*, 4(2), (2005), 218-224.

Shnyakina, G. P., et al., "Effect of Phenolic Compounds from Plants of the Genus Sedum and Their Antimicrobial Properties", *Database CA Online, Chemical Abstracts Service*, Columbus, Ohio, US, (May 12, 1984), 1 pg., abstract only.

Shukla, Y. N., "Bioactive Constituents from Oenothera Biennis Roots", *Abstract & Medicinal and Aromatic Plants Abstracts*, 26(1), (Feb. 2004), 1 pg., Abstract only.

Tissera, M. H., et al., "Toxicity Study of Baraka Oil (Oil of Nigella Sativa)", http://www.barkaoil.com/English/research_data/inside/toxicology_stu/toxicology_study.html,(Feb. 1996),4 pgs.

Tripathi, S. C., et al., "Fungitoxic Properties of Rosa Chinensis Jacq.", *Experientia*, 33(2), (Feb. 1977), 207-209.

Wise, Gilbert J., "Genitourinary Fungal Infections: a Therapeutic Conundrum", *Expert Opinion on Pharmacotherapy*, 2(8), (2001), 1211-1226.

* cited by examiner

ANTI-MICROBIAL COMPOSITION AND METHODS OF USE THEREOF

FIELD OF THE INVENTION

The invention relates to anti-microbial compositions and methods for treating yeast and fungal infections.

BACKGROUND OF THE INVENTION

Some of the most common pathogens associated with invasive fungal infections are the opportunistic yeasts, such as *Candida* spp. and *Aspergillus* spp. Thousands of *Candida* spp. cells can be present in an individual, primarily in the gastrointestinal tract, as a harmless commensal organism. However, *Candida* spp., such as *C. albicans,* cause opportunistic fungal infections. Infections can be localized, such as a vaginal infection or an oral infection, both of which cause a considerable degree of discomfort. In patients whose immune system is severely compromised (for example, prematurely born infants, patients infected with HIV, patients with hematological disease or cancer, and burn patients), the yeast can turn into a deadly pathogen causing systemic infections. *Aspergillus* spp., such as *A. niger,* are also opportunistic fungi which under certain conditions lead to infection, e.g., aspergillosis.

Currently available drugs for the treatment of fungal infections include amphotericin B, a macrolide polyene that interacts with fungal membrane sterols, flucytosine (5FC), a fluoropyrimidine that interferes with fungal protein and DNA biosynthesis, and a variety of azoles (e.g., triazoles and imidazoles such as ketoconazole, itraconazole, and fluconazole) that inhibit fungal membrane-sterol biosynthesis. Even though amphotericin B has a broad range of activity and is viewed as the "gold standard" of anti-fungal therapy, its use is limited due to infusion-related reactions and nephrotoxicity. Flucytosine usage is also limited due to the development of resistant microbes and its narrow spectrum of activity. The widespread use of azoles is causing the emergence of clinically-resistant strains of *Candida* spp.

The development of new anti-fungal treatment regimens has been a continuing challenge. What is needed in the art are additional anti-microbial, e.g., anti-fungal agents.

SUMMARY OF THE INVENTION

The present invention provides a pharmaceutical composition is provided comprising a pharmaceutically acceptable carrier and an effective amount of an agent, for example, a natural agent, selected from the group consisting of gallic acid, eucalyptol, naringin, a jasmonic acid compound, for example, methyl jasmonate, a derivative thereof, or a salt thereof, and any combination thereof. In one embodiment, the composition is formulated for systemic, local, topical, mucosal, oral, vaginal, pulmonary, nasal or ophthalmic administration. In one embodiment, the effective amount of the agent is a concentration of about 0.05 to 5.0% (by weight), for example, about 0.1 to 2.0% (by weight). In another embodiment, the composition comprises one or more additional ingredients, such as a topical anesthetic, an antimicrobial compound, an antifungal compound, a particulate material, a moisturizer, or a thickening agent. In certain embodiments of the invention, the agent selectively inhibits a fungus and/or a yeast, such as but not limited to a *Candida* spp. or an *Aspergillus* spp. In yet another embodiment, the agent does not inhibit a lactobacilli.

The present invention also provides a method of treating an infection, for example, an infection comprising *Candida* spp. or *Apergillus* spp., in a mammal comprising administering to the mammal a composition comprising a pharmaceutically acceptable carrier and an effective amount of a natural agent selected from the group consisting of gallic acid, eucalyptol, naringin, a jasmonic acid compound, e.g., methyl jasmonate, a derivative thereof, or a salt thereof, and any combination thereof. In one embodiment, the mammal is a human. In one embodiment of the method, the infection is a topical, nasal, mucosal, oral, vaginal, pulmonary, ophthalmic, local or systemic infection. In another embodiment of the method, the composition is formulated for local, systemic, topical, mucosal, oral, vaginal, pulmonary, nasal or ophthalmic administration. In one embodiment, the composition does not inhibit lactobacilli present in the mammal following administration of the composition. For example, in additional embodiments, *Candida* spp. and/or *Aspergillus* spp. that are present in the mammal are selectively inhibited following administration of the composition.

The invention further provides a method of treating a *Candida albicans* infection in a mammal, which method comprises administering to the mammal a composition comprising a pharmaceutically acceptable carrier and an effective amount of a natural anti-yeast agent selected from the group consisting of gallic acid, eucalyptol, naringin and any combination thereof. In another embodiment, the composition further comprises a jasmonic acid compound, for example, methyl jasmonate, a derivative thereof, or a salt thereof. In one embodiment, the mammal is a human. In one embodiment, the infection is a topical, mucosal, oral, vaginal, or systemic infection. In another embodiment, the composition is formulated for topical, mucosal, oral, vaginal, or systemic administration. In one embodiment, *C. albicans* is selectively inhibited in the mammal following administration of the composition. In yet another embodiment, the composition does not inhibit the lactobacilli present in the mammal following administration of the composition.

The invention additionally provides a method for treating a *Candida albicans* infection and an *Aspergillus niger* infection in a mammal, which method comprises administering to the mammal a composition comprising a pharmaceutically acceptable carrier and an effective amount of a natural agent comprising a jasmonic acid compound, e.g., methyl jasmonate, a derivative thereof, or a salt thereof. In one embodiment, the composition does not inhibit the lactobacilli present in the mammal following administration of the composition. In one embodiment, the mammal is a human. In another embodiment, the infection is a pulmonary infection. In yet another embodiment, *Candida albicans* and *Aspergillus niger* are selectively inhibited in the mammal following administration of the composition.

DETAILED DESCRIPTION OF THE INVENTION

Definitions

By "anti-fungal agent" or "anti-fungal compound" is meant an agent that reduces or inhibits, e.g., kills, fungal growth by at least 10%. For example, an anti-fungal agent of the invention may be "fungistatic" and/or "fungicidal." An "anti-yeast agent" or "anti-yeast compound" is an agent that reduces the growth of or inhibits, e.g., kills, yeast by at least 10%.

A "natural compound" or "natural agent" is a plant-based, animal-based, microorganism-based, soil-based or mineral-based compound. A natural compound is capable of being found in plants, animals, microorganisms, soils, or minerals. Examples of natural antimicrobials are known to the art and include phenolics (including simple phenols such as catechol and epicatechin; phenolic acids such as cinnamic acid; quinones such as hypericin; flavenoids such as chrysin and coumerins such as warfarin); terpenoids (including capsaicin); alkaloids (such as berberine) and lectins and polypeptids (including mannose-specific agglutinin) (Cowan, *Clinical Microbiology Reviews*, 12: 564-582 (1999)).

"Yeasts" and "fungi" belong to the kingdom Fungi, which includes eukaryotic microorganisms that can reproduce sexually (exchange nuclear material) or asexually (budding yeast). Fungi have a thick cell wall structure composed of complex carbohydrate polymers such as chitin-chitosan, glucan or mannan. Other morphological features include the development of cellular elongation or threads known as hyphae or mycelia. Some fungal species can develop spores that enable them to survive environmental changes such as heat, humidity and soil salinity. Variation in morphology is related to fungal species and environmental factors such as temperature, pH and nutrients. Yeasts are unicellular organisms, and reproduce by dividing, i.e., by budding or fission.

"Pathogenic fungi" include fungi that can cause disease in humans and have two primary morphological appearances. More than 100 species of fungi have pathogenic potential for humans. Their complex cell wall provides a protective covering that have made fungi impervious to many antimicrobial agents. Disease presentation can often be caused by morphological manifestation of fungus. For example, fungal mycelia will develop into fungal "bezoars" that can obstruct, for example, the urinary system. Budding yeast forms can be associated with infection or abscess.

By "fungal infection" or "mycoses" is meant an invasion of a host animal by fungal cells. For example, the infection may include the excessive growth of fungi that are normally present in or on the animal, or growth of fungi that are not normally present in or on the animal. More generally, a fungal infection can be any situation in which the presence of a fungal population is detrimental or damaging to a host animal. As used herein, "fungal infection" includes a primary fungal infection as well as an opportunistic fungal infection.

By "an effective amount" is meant an amount of a compound, in a combination of the invention, required to treat, prevent, delay the onset of or inhibit the progression of a fungal infection. The effective amount of active compound(s) used to practice the present invention for therapeutic or prophylactic treatment of conditions caused by or contributed to by a fungal infection varies depending upon the manner of administration, the age, body weight, and general health of the subject. Ultimately, the attending physician or veterinarian will decide the appropriate amount and dosage regimen. Such amount is referred to as an "effective" amount.

As used herein, the term "treat," "treated," or "treating" when used with respect to an disorder such as an infectious disease refers to a prophylactic treatment that increases the resistance of a subject to development of the disease (e.g., to infection with a pathogen) or, in other words, decreases the likelihood that the subject will develop the disease (e.g., become infected with the pathogen) as well as a treatment after the subject has developed the disease in order to fight the disease (e.g., reduce or eliminate at least one symptom typically associated with the infection) or prevent the disease from becoming worse.

Anti-Fungal Agents of the Invention

In some embodiments of the invention, pharmaceutical compositions are provided. In one embodiment, the pharmaceutical composition comprises a pharmaceutically acceptable carrier, and a natural antimicrobial compound as described herein, such as gallic acid, eucalyptol compound, naringin compound, methyl jasmonate compound or any combination thereof.

Gallic Acid

Gallic acid (GA) (3,4,5-trihydroxybenzoic acid, $C_6H_2(OH)_3CO_2H$) is a naturally occurring polyphenolic antioxidant. It is a colorless crystalline organic acid found in gallnuts, Sumac, tea leaves, oak bark, and many other plants, both in its free state and as part of the tannin molecule. Gallic acid has hydroxyl groups and a carboxylic acid group in the same molecule, thus two molecules can react with one another to form an ester, digallic acid. Gallic acid is obtained by the hydrolysis of tannic acid with sulfuric acid. Salts of gallic acid include any physiologically acceptable salt available to one of skill in art. Examples include sodium, calcium or potassium salts of gallic acid.

When present in the compositions of the present invention, gallic acid or its derivatives can be used in an amount of from about 0.001% to about 50%, or from about 0.01% to about 20%, or from about 0.01% to about 10%, or from about 0.05% to about 5%, or from about 0.05% to about 2% of the composition. According to the invention, in situ concentrations of gallic acid that range from about 0.1 to 2% (by weight) are effective for treating or preventing fungal infection in a subject.

Eucalyptol

Eucalyptol (1,3,3-Trimethyl-2-oxabicyclo[2,2,2]-octane; 1,8-epoxy-p-menthane; cineole; cajeputol) is a volatile, terpene-like oil extracted from the eucalyptus, and consisting largely of cymene. Salts of eucalyptol include any physiologically acceptable salt available to one of skill in art. Examples include sodium, calcium or potassium salts of eucalyptol.

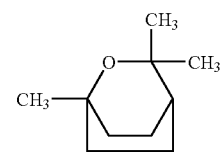

I

When present in the compositions of the present invention, eucalyptol or its derivatives can be used in an amount of from about 0.001% to about 50%, or from about 0.01% to about 20%, or from about 0.01% to about 10%, or from about 0.05% to about 5%, or from about 0.05% to about 2% of the composition. According to the invention, in situ concentrations of eucalyptol acid that range from about 0.1 to 2% (by weight) are effective for treating or preventing fungal infection in a subject.

Naringin

Naringin (7-[[2-O-(6-Deoxy-α-L-mannopyrano-syl)-β-D-glucopyranosyl]oxy]-2,3-dihydro-5-hydroxy-2-(4-hydroxyphenyl)-4H-1-benzopyran-4-one; 4',5,7-trihydroxyflavanone 7-rhamnoglucoside; naringenin-7-rhamnoglucoside; aurantiin) is a flavonoid compound found in grapefruit. See U.S. Pat. Nos. 2,421,062 and 2,421,063. Salts of naringin include any physiologically acceptable salt available to one of skill in art. Examples include sodium, calcium or potassium salts of naringin.

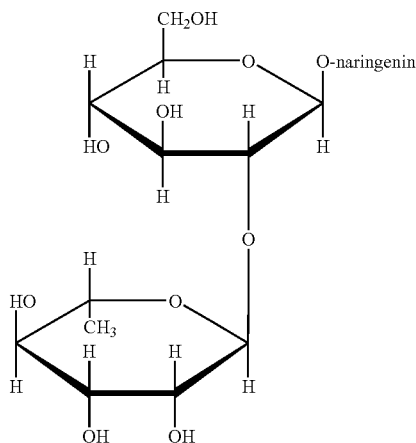

When present in the compositions of the present invention, naringin or its derivatives can be used in an amount of from about 0.001% to about 50%, or from about 0.01% to about 20%, or from about 0.01% to about 10%, or from about 0.05% to about 5%, or from about 0.05% to about 2% of the composition. According to the invention, in situ concentrations of naringin that range from about 0.1 to 2% (by weight) are effective for treating or preventing fungal infection in a subject.

Jasmonic Acid Compounds

Jasmonic acid compounds employed in the invention include jasmonic acid and jasmonic acid derivatives available to one of skill in the art. Such compounds include jasmonic acid, methyl jasmonate and their isomers. In the present invention jasmonic acid and jasmonic acid derivatives used also include synthetic and natural stereoisomers of jasmonic acid, dihydrojasmonic acid, hydroxyjasmonic acid and dihydro-hydroxy jasmonic acid. Further examples of jasmonic acid derivatives that may be used in the invention include compounds having any one of formulae III:

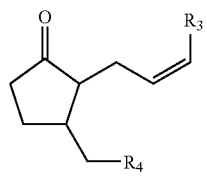

wherein:

$R_3$ is alkyl;

$R_4$ is COOR, or —$(CH_2)_n$—OX, where n is an integer of from 1 to 20;

R is H, or alkyl; and

X is H, or 1 to 6 sugar residues (e.g., hexose or pentose).

In general, the alkyl groups employed in these jasmonic acid compounds have about one to twenty carbon atoms, although in some embodiments lower alkyl groups are used, for example, alkyl groups with about one to eight carbon atoms. Alkyl groups with even lower numbers of carbon atoms can also be used, for example, alkyl groups with one to six, or one to three carbon atoms.

As used herein, lower alkyl means $(C_1\text{-}C_6)$ alkyl. Such $(C_1\text{-}C_6)$ alkyl can be methyl, ethyl, propyl, isopropyl, butyl, iso-butyl, sec-butyl, pentyl, 3-pentyl, or hexyl. Exemplary lower alkyl groups are $(C_1\text{-}C_3)$ alkyl including methyl ethyl, propyl, isopropyl and the like. Lower alkoxy generally means $(C_1\text{-}C_6)$ alkoxy; such $(C_1\text{-}C_6)$ alkoxy can, for example, be methoxy, ethoxy, propoxy, isopropoxy, butoxy, iso-butoxy, sec-butoxy, pentoxy, 3-pentoxy, or hexyloxy. Lower hydroxy alkyl refers to a hydroxy group attached to a lower alkyl or lower alkylene group (e.g. —$CH_2$—$CH_2$—OH). Lower alkanoyloxy refers to $(C_2\text{-}C_6)$alkanoyloxy, for example, acetoxy, propanoyloxy, butanoyloxy, isobutanoyloxy, pentanoyloxy, or hexanoyloxy. Lower $(C_1\text{-}C_6)$ alkanoylamino can, for example, be acetamino, propanoylamino, butanoylamino, isobutanoylamino, pentanoylamino, or hexanoylamino.

In some embodiments, jasmonic acid is employed in the compositions of the invention. Jasmonic acid is a compound of formula III wherein $R_3$ is $C_2H_5$ and $R_4$ is COOH.

Another jasmonic acid compound employed in the invention is a compound of formula IV.

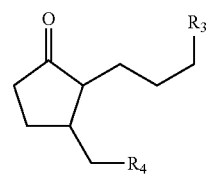

wherein:

$R_3$ is alkyl;

$R_4$ is COOR, or —$(CH_2)_n$—OX, where n is an integer of from 1 to 20;

R is H, or alkyl; and

X is H, or 1 to 6 sugar residues (e.g., hexoses or pentoses).

In some embodiments, dihydrojasmonic acid is employed in the compositions of the invention. Dihydrojasmonic acid is a compound of formula IV wherein $R_3$ is $C_2H_5$ and $R_4$ is COOH.

Another jasmonic acid compound employed in the invention is a compound of formula V.

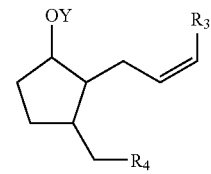

wherein:

$R_3$ is alkyl;

$R_4$ is COOR, or —$(CH_2)_n$—OX, where n is an integer of from 1 to 20;

R is H, or alkyl;

X is H, or 1 to 6 sugar residues (e.g., hexoses or pentoses); and

Y is H, alkyl, or 1 to 6 sugar residues (e.g., hexoses or pentoses).

In some embodiments, hydroxyjasmonic acid is employed in the compositions of the invention. Hydroxyjasmonic acid is a compound of formula VI wherein $R_3$ is $C_2H_5$ and $R_4$ is COOH.

Another jasmonic acid compound employed in the invention is a compound of formula VII.

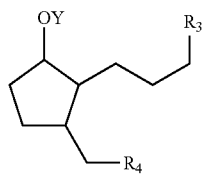

VII wherein:

$R_3$ is alkyl;

$R_4$ is COOR, or $-(CH_2)_n-OX$, where n is an integer of from 1 to 20;

R is H, or alkyl;

X is H, or 1 to 6 sugar residues (e.g., hexoses or pentoses); and

Y is H, alkyl, or 1 to 6 sugar residues (e.g., hexoses or pentoses).

In some embodiments, dihydro-hydroxyjasmonic acid is employed in the compositions of the invention. Dihydro-hydroxyjasmonic acid is a compound of formula VII wherein $R_3$ is $C_2H_5$ and $R_4$ is COOH.

In one embodiment of the invention, the jasmonic acid compound is a compound of formula VIII.

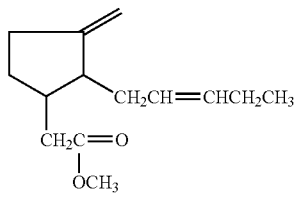

VIII

In some embodiments of the invention, the pharmaceutical composition comprises a salt of a jasmonic acid compound of the invention, which include any physiologically acceptable salt available to one of skill in art. Examples include sodium, calcium or potassium salts of a jasmonic acid compound.

When present in the compositions of the present invention, jasmonic acid compounds or derivatives thereof can be used in an amount of from about 0.001% to about 50%, or from about 0.01% to about 20%, or from about 0.01% to about 10%, or from about 0.05% to about 5%, or from about 0.05% to about 2% of the composition. According to the invention, in situ concentrations of jasmonic acid ranging from about 0.1 to 2% (by weight) are effective for treating or preventing a fungal infection in a subject.

The natural anti-fungal agents of the invention may optionally be delivered with other anti-microbial agents, for example, in the form of an anti-fungal cocktail, or individually, yet close enough in time to have a synergistic effect on the treatment of the infection. An anti-fungal cocktail is a mixture of any one of the above-described natural anti-fungal compounds with another anti-fungal drug that may or may not be a compound of the invention. The formulation of such cocktails in pharmaceutical preparations is routine. In this embodiment, a common administration vehicle (e.g., tablet, implants, injectable solution, injectable liposome solution, etc.) could contain both the compound of the invention and the other anti-fungal agent(s). Such antimicrobial agents are useful for the treatment and prevention of infective fungi, and are known to the art.

Assays for evaluating the anti-fungal properties of compositions of the invention are well known to the art. In vitro experiments can be conducted using pure substances or crude extracts of natural compounds. For example, zone of inhibition tests can be conducted, such as the ASTM E2149-01 test (the Standard Test Method for Determining the Antimicrobial Activity of Immobilized Antimicrobial Agents Under Dynamic Contact Conditions) or a modified ASTM E2149-01 test.

In addition, a procedure for Determining the Presence of Leaching Antimicrobial can be performed (see section 12 of ASTM E2149-01). In one embodiment of the invention, antimicrobial compounds were evaluated using a modified procedure, for example, instead of processing the materials (liquids), they were placed into 8 mm holes bored into an agar plate and inoculated with a test organism. The antimicrobial compounds (liquids) were placed into the bored holes (100 µl volumes), incubated for 24 hours, and then checked for clearing zones of inhibition (microbial kill).

METHODS OF THE INVENTION

As described herein, the compounds and compositions of the present invention may be used to treat a variety of fungal infections and diseases associated with such infections, such as Aspergillosis, Candidiasis, as well as an infection caused by rare and unusual fungi. In methods described herein for treating fungal infections, a subject in need of such treatment is administered a composition described herein in an amount effective to treat the fungal infection. The subject can be a human, non-human primate, or other mammal, such as but not limited to dog, cat, horse, cow, pig, turkey, goat, fish, monkey, chicken, rat, mouse, and sheep.

Fungal infections (mycoses) can cause conditions including the following: tinea capitis, tinea corporis, tinea pedis, tinea barbae, tinea cruris, tinea versicolor, onychomycosis, perionychomycosis, pityriasis versicolor, tinea unguium, oral thrush, vaginal candidosis, respiratory tract candidosis, biliary candidosis, eosophageal candidosis, urinary tract candidosis, systemic candidosis, mucocutaneous candidosis, mycetoma, cryptococcosis, aspergillosis, mucormycosis, chromoblastomycosis, paracoccidioidomycosis, North American blastomycosis, histoplasmosis, coccidioidomycosis, or sporotrichosis. In addition, diseases caused by fungal infection include "systemic mycoses." These fungal infections are generalized throughout the body. Often, systemic infections are acquired via inhalation of airborne spores and initiated in the lungs. Examples of systemic infections include mucocutaneous candidosis, chromoblastomycosis, mycetoma, cryptococcosis, aspergillosis, mucormycosis, paracoccidioidomycosis, North American blastomycosis, histoplasmosis, coccidioidomycosis (San Joaquin or valley fever), and sporotrichosis. As with most systemic pathogens, if left untreated, serious life-threatening infections can develop.

In some embodiments of the invention, the subject is an immunocompromised host, for example, those infected by HIV, those undergoing chemotherapy, transplant recipients, or cancer patients receiving immunosuppressive medications. In some embodiments of the invention, the subject is a premature or low birthweight infant.

The basis for the definite diagnosis of an invasive fungal infection is the detection of fungal pathogens in sterile body fluids (e.g., blood culture, CNS fluid, bronchoalveolar lavage) and/or tissue samples (e.g., skin, lung, liver, or from other organs) by a mycological culture together with the histological detection of the fungus in tissue. Invasive candidiasis may present only with fever not responding to broad-spectrum antibacterials without any further typical signs. Blood culture remains the most important source for the detection of *Candida* species as well as other yeasts, e.g., *Cryptococcus neoformans,* from the blood. In the last 12 years the use of PCR technology was introduced to detect invasive candidiasis or aspergillosis. Various studies suggest good sensitivity and specificity as well as positive correlation with clinical outcome. Common approaches consist either of a nested PCR design or a "Panfungus"-PCR with "unspecific" primers which amplifies first a sequence within the small 18S ribosomal unit RNA of most fungal pathogens followed by hybridization with species-specific probes.

Exemplary Fungal Infections Amenable to the Methods of the Invention

Aspergillosis

The term "aspergillosis" encompasses a variety of disease processes caused by *Aspergillus* species. The types of diseases caused by *Aspergillus* spp. are varied, ranging from an allergy-type illness to life-threatening generalized infections. Diseases caused by *Aspergillus* are called aspergillosis. Of the more than 300 species of *Aspergillus* known, only some are ordinarily pathogenic for humans, including: *A. fumigatus, A. flavus, A. niger, A. nidulans, A. terreus, A. sydowi, A. flavatus,* and *A. glaucus.* Aspergillosis is increasing in prevalence and is particularly a problem among patients with chronic respiratory disease or immunocompromised patients. *Aspergillus fumigatus* and *A. flavus* account for >90% of cases of invasive aspergillosis.

There has been an increasing incidence of invasive aspergillosis for a variety of reasons (e.g., AIDS, intensive chemotherapy for malignancies, solid organ transplants, increased use of immunosuppressive regimens for autoimmune diseases). The primary portal of entry of Aspergilla is through the respiratory system or by direct invasion of tissue via intravascular catheter, surgery or inflamed tissue, i.e., keratitis. Typical clinical manifestations of aspergillosis include pulmonary (80-90% of infections) followed by sinus (5-10% of infections) and brain (5-10% of infections). In the pre-AIDS era, renal involvement was observed in 13% of postmortem patients with systemic aspergillosis. Renal infections have been reported in patients who are immunocompromised by diabetes mellitus, malignancy, immunesuppression or AIDS.

Among immunocompromised patients, aspergillosis is second only to candidiasis as the most common opportunistic mycosis and accounts for about 15% of the systemic mycoses in this group. Opportunistic pulmonary aspergillosis is characterized by widespread bronchial erosion and ulceration, followed by invasion of the pulmonary vessels, with thrombosis, embolization and infarction. Clinically, infection manifests as a necrotizing patchy bronchopneumonia, sometimes with hemorrhagic pulmonary infarction. In about 40% of cases, there is hematogenous spread to other sites. Aspergillosis is also a rare but devastating complication of traumatic wounds, such as, burn wounds, frost bite wounds, or wounds developed by diabetics, where amputation is often required.

*Aspergillus* species are ubiquitous, and their spores are constantly being inhaled. Decomposing vegetation, potted plants, spices and even marijuana may yield Aspergilla. Nosocomial Aspergilla infections have been associated with hospital construction. Detection of *Aspergillus* infection is difficult as blood, urine and cerebrospinal fluid cultures are rarely positive, however, the fungi can be seen in smears and biopsies from infected tissue. Most clinical microbiological laboratories can identify common species of Aspergilla on standard bacteriological and fungal media. Molecular methods (e.g., ELISA) can be utilized to test serum or other fluids for Aspergilla galatomannan or circulating 1,3-β-D-glucan (G-test). However, these serological tests are not very sensitive or specific. Invasive Aspergilia infection will result in dissemination and death unless treated promptly.

In one embodiment of the invention, a method for treating a fungal infection caused by an *Aspergillus* spp. by administering a composition of the invention is provided. In one embodiment of the invention, this treatment involves localized administration of a pharmaceutical composition of the invention to the lungs of a subject, for example, intranasally or oral inhalation.

Candidiasis

In some embodiments of the present invention, a fungal infection caused by a fungus of the *Candida* genus is treated. In one embodiment, the yeast is of the *Candida albicans* species. In other embodiments, the *Candida* yeast may be of the *Candida dubliniensis, Candida parapsilosis, Candida tropicalis, Candida kefrr, Candida guilliermondii, Candida inconspicua, Candida famala, Candida glabrata, Candida krusei, Candida lusitaniae,* or other *Candida* species.

During a 7 year surveillance period (1986-1993), blood cultures in a 1000-bed tertiary care hospital identified 102 episodes of nosocomial fungaemia that represented 6.6% of blood borne infections (Wise, *Expert Opin. Pharmacother.,* 2:1211 (2001)). *C. albicans* represented 74% of infections followed by *C. glabrata* (8%), *C. parapsilosis* (7%), *C. tropicalis* (3%), *C. lusitaniae* (2%) and other fungi which included *C. krusei, Malasessia furfur, Saccahromyces cerevisiae, Histoplasma anomala* and *Cryptococcus albidis* (Id.).

The compositions of the invention may be used to prevent or treat a fungal infection such as systemic candidiasis in an immunocompromised host and in hosts suffering from acute leukemia. In such situations, administration of the composition can, for example, be oral, subcutaneous, intravenous or intramuscular and the composition can include antifungal drugs. Such infections are frequently life-threatening and are responsible for 10% of all nosocomial blood-stream infection. Y Cho and H Y Choi. *Opportunistic fungal infection among cancer patients. A ten year autopsy study.* Am. J. Clin. Pathol. 1991, 72:617-621.

The compositions of the invention may also be used to prevent or treat a fungal infection such as, for example, genital candidiasis. Genital candidiasis, generally known as yeast infection, is the infection of the genital tract caused by *Candida albicans.* Women suffering from yeast infection usually develop vulval irritation, itching and vaginal discharge, the vaginal wall is covered with a white cheesy material, and the vulva is reddish and swollen. Infections by *Candida albicans* can be inhibited and/or treated by the compositions and methods of the invention.

Diagnosis of a candida infection can be achieved by microscopic examination, which can reveal *Candida* fungi with budding forms of pseudohyphae. *Candida* spp. can be cultured from physiological fluids such as urine with a variety of laboratory media, including cysteine lactose electrolyte deficient, blood agar and Sabouraud's agar with dextrose. Species differentiation is dependent on germ tube growth and carbohydrate fermentation. The utilization of polymerase chain reaction (PCR) amplification has been helpful in the rapid detection of small numbers of *C. albicans*. Whole cell agglutination, agar cell diffusion, latex agglutination, counter-immune electrophoresis or radio-immunoassays have been utilized to assess patient antibody response to candidal antigen. PCR amplification of *Candida* gene components has proven efficacious in the detection of occult candidaemia in critically ill patients.

Other Fungal Infections

Infections caused by fungal species such as *Blastoschizomyces capitatus, Trichosporon, Fusarium* spp., *Geotrichum, Pseudallescheria boydii. Malassezia furfur* and *Cunninghamella* may be treated using the compositions and methods of the present invention. The pool of patients vulnerable to such infections includes patients with HIV, bone marrow and organ transplants, cancer patients with chemotherapy and premature infants.

Pharmaceutical Compositions, Dosages, and Routes of Administration

The pharmaceutical compositions of the invention can be administered for prophylactic, therapeutic, and/or hygienic use. Such administration can be topical, mucosal, e.g., oral, nasal, vaginal, rectal, parenteral, transdermal, subcutaneous, intramuscular, intravenous, via inhalation, ophthalmic and other convenient routes. The pharmaceutical compositions can be administered in a variety of unit dosage forms depending upon the method of administration. For example, unit dosage forms suitable for oral administration include powder, tablets, pills, capsules and lozenges.

The compositions for administration will commonly comprise a solution of an anti-fungal agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of anti-fungal agent in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.01 to about 100, or about 0.1 to about 10, mg per patient per day. Dosages from about 0.1 mg, up to about 1000 mg, per patient per day may be used, particularly when administered to a secluded site and not into the blood stream, such as into a body cavity or into a lumen of an organ. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980).

The compositions containing the anti-fungal agent(s) can be administered for therapeutic treatments. In therapeutic applications, compositions are administered to a patient suffering from a disease, e.g., a fungal infection, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the anti-fungal agent(s) of the invention to effectively treat the patient.

The therapeutic composition of the invention can be combined for therapeutic use with additional active ingredients, e.g., in conventional pharmaceutically acceptable carriers or diluents, along with physiologically innocuous stabilizers and excipients; see Berkow (Ed.), *The Merck Manual,* Merck, Rahway, N.J. These combinations can be filtered sterile and placed into dosage forms as by lyophilization in dosage vials or storage in stabilized aqueous preparations.

The quantities of reagents necessary for effective therapy depend upon many different factors, including means of administration, target site, physiological state of the patient, and other medicaments administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman et al. (Eds.), (1990) *Goodman and Gilman's: The Pharmacological Basis of Therapeutics,* 8th ed., Pergamon Press, Tarrytown, N.Y., and in *Remington's Pharmaceutical Sciences,* 17th ed. (1990), Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers may include water, saline, buffers, and other compounds described, e.g., in *The Merck Index,* Merck & Co., Rahway, N.J. See also (e.g.) Avis et al. (Eds.), (1993) *Pharmaceutical Dosage Forms: Parenteral Medications,* Dekker, New York, and Leiberman et al. (Eds.), (1990) *Pharmaceutical Dosage Forms: Disperse Systems,* Dekker, New York. Slow-release formulations or slow-release apparatus may be utilized for continuous administration.

Therapeutic formulations may be administered in any conventional dosage formulation. Whereas it is possible for the active ingredient to be administered alone, it is preferable to present it as a pharmaceutical formulation. Formulations comprise at least one active ingredient, together with one or more acceptable carriers therefor. Each carrier must be both pharmaceutically and physiologically acceptable in the sense of being compatible with the other ingredients and not injurious to the patient. Formulations include those suitable for mucosal, e.g., oral, vaginal, topical, rectal, nasal, or parenteral administration (including subcutaneous, intramuscular, intravenous and intradermal administration). The formulations may conveniently be presented in unit dosage form and may be prepared by any methods well known in the art of pharmacy: e.g., Gilman et al. (Eds.), (1990) *Goodman and Gilman's: The Pharmacological Basis of Therapeutics,* 8th ed., Pergamon Press; and *Remington's Pharmaceutical Sciences,* 17th ed. (1990), Mack Publishing Co., Easton, Pa. Further, the invention may be combined with or used in association with other chemotherapeutic or chemopreventive agents.

Therapeutic compositions according to the invention may be formulated into topical preparations for local therapy by including a therapeutically effective concentration of the anti-fungal agent(s) in a mucosal or dermatological vehicle. The amount to be administered, and the concentration in the topical formulations, depend upon the vehicle selected, the clinical condition of the patient, the systemic toxicity and the stability of the formulation. Thus, a physician knows to employ the appropriate preparation containing the appropriate concentration of therapeutic agents in the formulation, as well as the appropriate amount of formulation to administered depending upon clinical experience with the patient in question or with similar patients. The concentration of therapeutic compositions for mucosal or topical formulations is in the range of greater than from about 0.1 mg/ml to about 25 mg/ml. Typically, the concentration of the agents in the composition for topical formulations is in the range of greater than from about 1 mg/ml to about 20 mg/ml. Solid dispersions of the compositions according to the invention, as well as solubilized preparations, may be used. Thus, the precise concentration to be used in the vehicle is subject to modest experimental manipulation in order to optimize the therapeutic response. For example, greater than about 10 mg anti-fungal agent/100 grams of vehicle may be useful with 1% w/w hydrogel vehicles. Suitable vehicles, in addition to gels, are oil-in-water or water-in-oil emulsions using mineral oils, petroleum and the like.

Mucosal or topical preparations of the therapeutic composition either for systemic or local delivery may be employed and may contain excipients as described above for parenteral administration and other excipients used in a topical preparation such as cosolvents, surfactants, oils, humectants, emollients, preservatives, stabilizers and antioxidants. Pharmacologically acceptable buffers may be used, e.g., Tris or phosphate buffers. The topical formulations may also optionally include one or more agents variously termed enhancers, surfactants, accelerants, adsorption promoters or penetration enhancers, such as an agent for enhancing percutaneous penetration of the therapeutic composition or other agents. Such agents should desirably possess some or all of the following features as would be known to the ordinarily skilled artisan: pharmacological inertness, non-promotive of body fluid or electrolyte loss, compatible with the therapeutic composition (non-inactivating), and capable of formulation into creams, gels or other topical delivery systems as desired.

Topical preparations are applied daily directly to the skin or mucosa and are then preferably occluded, i.e., protected by overlaying a bandage, polyolefin film or other barrier impermeable to the topical preparation.

Alternatively, the composition of the invention may be administered orally. Typically, a therapeutically effective oral dose of a composition according to the invention is in the range from about 0.05 mg/kg body weight to about 50 mg/kg body weight per day. In one embodiment, an effective dose is in the range from about 0.05 mg/kg body weight to about 5 mg/kg body weight per day.

In one embodiment, the pharmaceutical composition is administered vaginally. For intravaginal administration, the therapeutic agents may be formulated as is known in the art for direct application to the vaginal area. Forms chiefly conditioned for vaginal application take the form, for example, of creams, milks, geis, dispersion or micro-emulsions, lotions thickened to a greater or lesser extent, impregnated pads, ointments, aerosol formulations (e.g., sprays or foams), creams, lotions, pastes, jellies, sprays, and aerosols. Alternatively, the composition can be formulated to be part of an adhesive polymer, such as polyacrylate or acrylate/vinyl acetate copolymer. The dose will be dependent upon the properties of the specific composition employed, e.g., its activity and biological half-life, the concentration of composition in the formulation, the site and rate of dosage, the clinical tolerance of the patient involved, the disease afflicting the patient and the like, as is well within the skill of the physician.

In addition, the compositions of the invention may be administered to the lung(s) of a subject by any suitable means, e.g., be inhaled into a patient's respiratory tract and lungs through the nose or mouth. The composition of the invention can be aerosolized in a variety of forms, such as, but not limited to, dry powder inhalants, metered dose inhalants, or liquid/liquid suspensions. When administered by inhalation, carriers such as polyethylene glycol or glycols, DPPC, methylcellulose, powdered dispersing agents can be used. In some embodiments of the invention, a composition of the invention is administered by inhalation, for example, in a nebulized form. For example, delivery may be by use of a single-use delivery device, a mist nebulizer, a breath-activated powder inhaler, an aerosol metered-dose inhaler (MDI) or any other of the numerous nebulizer delivery devices available in the art. Additionally, mist tents or direct administration through endotracheal tubes may also be used. In addition, delivery via an intratracheal or nasopharyngeal mode will be efficacious for certain indications. The dose will be dependent upon the properties of the specific composition employed, e.g., its activity and biological half-life, the concentration of composition in the formulation, the site and rate of dosage, the clinical tolerance of the patient involved, the disease afflicting the patient and the like, as is well within the skill of the physician.

The compositions of the present invention may be administered in solution. The compositions thereof may be in a solution having a suitable pharmaceutically acceptable buffer such as phosphate, Tris(hydroxymethyl)aminomethane-HCl or citrate and the like. Buffer concentrations should be in the range of 1 to 100 mM. The composition solution may also contain a salt, such as sodium chloride or potassium chloride in a concentration of 50 to 150 mM. An effective amount of a stabilizing agent such as an albumin, a globulin, a gelatin, a protamine or a salt of protamine may also be included, and may be added to a solution containing composition or to the composition from which the solution is prepared.

The compositions of the invention can be administered in the form of an article or carrier such as a bandage, insert, syringe-like applicator, tablet, suppository, pessary, powder/talc or other solid, solution, liquid, spray, aerosol, douche, ointment, tampon, foam, cream, gel, paste, microcapsules, vaginal sponge, vaginal ring, controlled release formulation, sustained release formulation or bioadhesive gel (e.g., a mucoadhesive thermogelling composition (see, for example, U.S. application Ser. No. 10/135805, filed on Apr. 30, 2002, which is incorporated herein by reference)).

The term "unit dosage" and its grammatical equivalents as used herein refer to physically discrete units suitable as unitary dosages for human patients and other warm blooded animals, each unit containing a predetermined effective and potentiating amount of at least one of the two active ingredients calculated to produce the desired therapeutic effect in association with the required physiologically tolerable carrier, e.g., a diluent or a vehicle. The specifications for the unit dosage forms of this invention are dictated by and are directly dependent on (a) the unique characteristics of the active ingredients and the particular therapeutic effect to be achieved, and (b) the limitations inherent in the art of compounding such as active ingredient for therapeutic use in humans and other animals. Examples of suitable unit dosage forms in accord with this invention are tablets, capsules, pills, powder packets, granules, wafers, and the like, segregated multiples of any of the foregoing, as well as liquid solutions, emulsions and suspensions. The amount of each active ingredient that is administered in vivo depends on the age and weight of the patient, the particular disease to be treated and its severity, the frequency of administration, and the route of administration.

In any treatment regimen, the therapeutic composition may be administered to a patient either singly or in a cocktail containing other therapeutic agents, compositions, or the like, including, but not limited to, immunosuppressive agents, tolerance-inducing agents, potentiators and side-effect relieving agents. Particularly preferred are immunosuppressive agents useful in suppressing allergic reactions of a host. Preferred immunosuppressive agents include prednisone, melphalain, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Preferred potentiators include monensin, ammonium chloride, perhexiline, verapamil, amantadine and chloroquine. All of these agents are administered in generally accepted efficacious dose ranges such as those disclosed in the Physician's Desk Reference, 41st Ed., Publisher Edward R. Barnhart, N.J. (1987).

EXAMPLES

Example 1

Natural compounds were evaluated for anti-microbial activity using the zone of inhibition test (ASTM E214901). The activity against five types of microorganisms: *Staphylococcus aureus, Pseudomonas aeruginosa, Escherichia coli, Aspergillis niger* and *Candida albicans*, was evaluated. These microorganisms represent gram positive and gram negative bacteria, fungi and yeast.

The compounds were tested for activity against *E. coli* (ATCC 8739; Gram negative bacteria), *S. aureus* (ATCC 6538; Gram positive bacteria), *P. aeruginosa* (ATCC 9027; Gram negative bacteria), *C. albicans* (ATCC 10231; yeast) and *A niger* (ATCC 16404; fungus) at 1 and 10 mg/ml concentrations by using the zone of inhibition method along with triclosan as a positive control.

Materials and Methods

Compounds Tested

The following natural compounds were tested for their anti-fungal properties: eucalyptol, cineole (SIGMA C-8144); gallic acid, 3,4,5-trihydroxybenzoic acid (SIGMA G-7384); methyl jasmonate, 95% (Aldrich 39270-7); and naringin: >95%, made from citrus fruit (SIGMA N-1376). A DMSO/water (75/25 by volume) mixture was used as the carrying solvent for each compound tested. The compounds were tested at 1 and 10 mg/ml concentrations by using the zone of inhibition method along with triclosan as a positive control.

Antimicrobial Screening Test Method: Zone-of-Inhibition Test

Microorganism cultures of $10^5$ cfu (colony forming units)/ml in a 1×PBS (phosphate buffered saline) solution were used. One ml of the solution was plated on a trypticase soy agar plate (TSA) and allowed to grow at 35° C. for four hours. 4 mm diameter wells were then punched in each TSA plate and 100 µl of each compound being tested was added to these wells. The plates were incubated overnight at 35° C. Lawn clearing was measured the next day as an indicator of antimicrobial activity.

Results

TABLE 1

Zone of inhibition test results in two concentrations against five microorganisms.

| Compound | Concentration (mg/ml) | S. aureus (mm) | P. aeruginosa (mm) | E. coli (mm) | C. albicans (mm) | A. niger (mm) |
|---|---|---|---|---|---|---|
| Triclosan |  | 10 | 0 | 11 | 8.5 | 10 |
| Gallic acid | 1 | 0 | 0 | 0 | 5 | 0 |
|  | 10 | 0 | 0 | 0 | 4 | 0 |
| Eucalyptol | 1 | 0 | 0 | 0 | 3 | 0 |
|  | 10 | 0 | 0 | 0 | 3 | 0 |
| Methyl jasmonate | 1 | 0 | 0 | 0 | 0 | 0 |
|  | 10 | 2 | 0 | 0 | 7.5 | 5 |
| Naringin | 1 | 0 | 0 | 0 | 3 | 0 |
|  | 10 | 0 | 0 | 0 | 3.5 | 0 |

Conclusion

Among the compounds tested, gallic acid, eucalyptol and naringin were found to be selective inhibitors of *C. albicans* with no effect on the other four organisms tested. In addition, methyl jasmonate was found to selectively inhibit both *C. albicans* and *A. niger*. Gallic acid, eucalyptol, naringin and methyl jasmonate can be effectively utilized to treat fungal infections, for example, of the mouth, skin and vagina.

Example 2

*C. albicans* is an opportunistic organism that can cause various infections of the skin, mouth and vagina. *C. albicans* and other *Candida* strains are part of normal human microbial flora, but under certain circumstances may cause complications, such as infection. The challenge to the medical field is to control the growth of *Candida* spp. without affecting the other organisms that make up normal human microflora.

As described herein, the present inventors discovered natural compounds that selectively inhibit *C. albicans* only. Five of these compounds were tested against *Lactobacillus acidophilus* (ATCC 11975). None of the compounds tested had antimicrobial activity against lactobacilli, a microorganism normally found in humans, specifically in the vagina. Due to their ability to derive lactic acid from glucose, these bacteria create an acidic environment that inhibits growth of many bacterial species that can lead to urogenital infections. *Lactobacillus* is generally harmless to humans, rarely inciting harmful infections or diseases. Thus, these compounds can be effectively utilized to develop products to address infections arising from *Candida, Aspergillus* and related species without destroying the normal balance of microbial species found in human gastrointestinal tract.

Materials and Methods

Gallic acid, 3,4,5-trihydroxybenzoic acid (SIGMA G-7384); eucalyptol, cineole (SIGMA C-8144); naringin: >95%, made from citrus fruit (SIGMA N-1376), and methyl jasmonate, 95% (Aldrich 39270-7) were tested in two concentrations (1 and 10 mg/ml) in DMSO:water (75:25) along with positive control (chlorhexidine 5 mg/ml in 75:25 DMSO:water) and a negative control (75:25 DMSO:water). All tests were conducted in duplicate in a zone of inhibition study (as described in Example 1).

TABLE 2

Zone of Inhibition test results in two concentrations against *Lactobacillus acidophilus*

| Sample # | Product code/ description | Inoculum Level | Zone of Inhibition | Sample Size |
|---|---|---|---|---|
| 1 | Methyl jasmonate 10 mg/ml | $5.8 \times 10^5$ CFU/ml | None | 100 μl |
|  | Methyl jasmonate 1 mg/ml | $5.8 \times 10^5$ CFU/ml | None | 100 μl |
|  | Negative Control | $5.8 \times 10^5$ CFU/ml | None | 100 μl |
|  | Positive control | $5.8 \times 10^5$ CFU/ml | 6 mm | 100 μl |
|  | Methyl jasmonate 10 mg/ml | $5.8 \times 10^5$ CFU/ml | None | 100 μl |
|  | Methyl jasmonate 1 mg/ml | $5.8 \times 10^5$ CFU/ml | None | 100 μl |
|  | Negative Control | $5.8 \times 10^5$ CFU/ml | None | 100 μl |
|  | Positive control | $5.8 \times 10^5$ CFU/ml | 6 mm | 100 μl |
| 2 | Naringin 10 mg/ml | $5.8 \times 10^5$ CFU/ml | None | 100 μl |
|  | Naringin 1 mg/ml | $5.8 \times 10^5$ CFU/ml | None | 100 μl |
|  | Negative Control | $5.8 \times 10^5$ CFU/ml | None | 100 μl |
|  | Positive control | $5.8 \times 10^5$ CFU/ml | 6 mm | 100 μl |
|  | Naringin 10 mg/ml | $5.8 \times 10^5$ CFU/ml | None | 100 μl |
|  | Naringin 1 mg/ml | $5.8 \times 10^5$ CFU/ml | None | 100 μl |
|  | Negative Control | $5.8 \times 10^5$ CFU/ml | None | 100 μl |
|  | Positive control | $5.8 \times 10^5$ CFU/ml | 6 mm | 100 μl |
| 3 | Gallic acid 10 mg/ml | $5.8 \times 10^5$ CFU/ml | None | 100 μl |
|  | Gallic acid 1 mg/ml | $5.8 \times 10^5$ CFU/ml | None | 100 μl |
|  | Negative control | $5.8 \times 10^5$ CFU/ml | None | 100 μl |
|  | Positive control | $5.8 \times 10^5$ CFU/ml | 6 mm | 100 μl |
|  | Gallic acid 10 mg/ml | $5.8 \times 10^5$ CFU/ml | None | 100 μl |
|  | Gallic acid 1 mg/ml | $5.8 \times 10^5$ CFU/ml | None | 100 μl |
|  | Negative control | $5.8 \times 10^5$ CFU/ml | None | 100 μl |
|  | Positive control | $5.8 \times 10^5$ CFU/ml | 6 mm | 100 μl |
| 4 | Eucalyptol 10 mg/ml | $5.8 \times 10^5$ CFU/ml | None | 100 μl |
|  | Eucalyptol 1 mg/ml | $5.8 \times 10^5$ CFU/ml | None | 100 μl |
|  | Negative control | $5.8 \times 10^5$ CFU/ml | None | 100 μl |
|  | Positive control | $5.8 \times 10^5$ CFU/ml | 6 mm | 100 μl |
|  | Eucalyptol 10 mg/ml | $5.8 \times 10^5$ CFU/ml | None | 100 μl |
|  | Eucalyptol 1 mg/ml | $5.8 \times 10^5$ CFU/ml | None | 100 μl |
|  | Negative control | $5.8 \times 10^5$ CFU/ml | None | 100 μl |
|  | Positive control | $5.8 \times 10^5$ CFU/ml | 6 mm | 100 μl |

Conclusion

The results presented in Table 2 indicate that these natural compounds have no antimicrobial activity against lactobacilli. However, as shown in Example 1, these compounds can be effectively utilized to treat fungal and yeast infections of mouth, skin and vagina. More particularly, they can be used to treat conditions where selective inhibitors are preferred over broad spectrum antimicrobials, and in particular, to selectively address infections arising from *Candida* spp. and *Aspergillus* spp. without affecting normal human microflora.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. An antifungal pharmaceutical composition comprising a pharmaceutically acceptable carrier and an effective amount of 0.1 to 2.0% naringin and 0.1 to 2.0% of a jasmonic acid compound (by weight) selected from the group consisting of jasmonic acid, methyl jasmonate and a salt thereof.

2. The composition of claim 1 formulated for systemic, local, topical, mucosal, oral, vaginal, pulmonary, nasal or ophthalmic administration.

3. The composition of claim 1, further comprising one or more additional ingredients.

4. The composition of claim 3, wherein the one or more additional ingredients are a topical anesthetic, an antimicrobial compound, an antifungal compound, a particulate material, a moisturizer, or a thickening agent.

* * * * *